United States Patent
Brancq et al.

Patent Number: 5,958,431
Date of Patent: Sep. 28, 1999

[54] USE OF FATTY ALCOHOL BASED COMPOSITIONS FOR PREPARING EMULSIONS; METHOD OF PREPARING EMULSIONS AND EMULSIONS SO OBTAINED

[75] Inventors: Bernard Brancq, Le Chesnay; Jean-Pierre Boiteux, Saix, both of France

[73] Assignee: Societe d'Exploitation de Produits pour les Industries Chimique S.E.P.P.I.C., Paris, France

[21] Appl. No.: 08/445,876

[22] Filed: May 22, 1995

Related U.S. Application Data

[63] Continuation of application No. 08/039,017, filed as application No. PCT/FR91/00804, Oct. 16, 1991, abandoned.

[30] Foreign Application Priority Data

Oct. 17, 1990 [FR] France .................... 90 12842

[51] Int. Cl.⁶ .................... A61K 7/00; A61K 7/02
[52] U.S. Cl. .................... 424/401; 424/70.1; 514/937; 514/938
[58] Field of Search .................... 424/401, 70.1; 514/937, 938

[56] References Cited

U.S. PATENT DOCUMENTS

| | | | |
|---|---|---|---|
| 3,547,828 | 12/1970 | Mansfield | 252/351 |
| 3,839,318 | 10/1974 | Mansfield | 260/210 R |
| 4,258,063 | 3/1981 | Chun | 424/365 |
| 4,472,170 | 9/1984 | Hellyer | 44/51 |
| 4,713,447 | 12/1987 | Letton | 536/18.6 |
| 4,798,682 | 1/1989 | Ansmann | 424/70 |
| 4,892,728 | 1/1990 | Kawa | 424/70 |
| 4,900,545 | 2/1990 | Wisotzki | 424/70 |
| 5,003,057 | 3/1991 | McCurry | 536/186 |
| 5,017,305 | 5/1991 | Hoeffkes | 252/311 |
| 5,306,442 | 4/1994 | Hill et al. | 252/131 |

FOREIGN PATENT DOCUMENTS

| | | |
|---|---|---|
| 77167 | 4/1983 | European Pat. Off. |
| 230598 | 8/1987 | European Pat. Off. |
| 336000 | 10/1989 | European Pat. Off. |
| 345586 | 12/1989 | European Pat. Off. |
| 1203036 | 8/1989 | Japan |

*Primary Examiner*—Sally Gardner-Lane
*Attorney, Agent, or Firm*—Ladas & Parry

[57] ABSTRACT

The present invention relates to the use of fatty alcohol based compositions comprising:
- 60 to 90% by weight of at least one fatty alcohol having from 12 to 22 carbon atoms, preferably from 16 to 18 carbon atoms,
- 10 to 40% by weight of an alkylpolyoside, preferably an alkylpolyoside of which the alkyl part is identical to that of the fatty alcohol,
- and, if appropriate, 0.5 to 5% of polyoside, for preparing emulsions.

The invention finds an application in particular for preparing emulsions in the cosmetic and pharmaceutical fields.

56 Claims, No Drawings

USE OF FATTY ALCOHOL BASED COMPOSITIONS FOR PREPARING EMULSIONS; METHOD OF PREPARING EMULSIONS AND EMULSIONS SO OBTAINED

This is a continuation of application Ser. No. 08/039,017 filed on Apr. 6, 1993 abandoned which was filed under 35 U.S.C. 371 from International Application PCT/FR91/00804 filed on Oct. 16, 1991, and which designated the U.S.

The present invention relates generally to the use of fatty alcohol based compositions for preparing emulsions; a method of preparing emulsions and the emulsions so obtained.

The invention finds a particular application in the cosmetic and pharmaceutical fields.

It is known that the emulsions generally used in the cosmetic and pharmaceutical fields essentially contain non-ionic emulsifiers of polyol ester or ether type (glycerol, sorbitol, glycol, polyglycerol, etc.), the function of which is to make the lipophilic fatty phases compatible with the aqueous phase.

It is also known that certain compositions, based on fatty alcohol, acid or ester, can be made self-emulsifiable by using, as emulsifier, an hydrophilic type surface-active product of non-ionic nature, obtained by grafting of a polyoxyethylated chain.

The expression "self-emulsifiable" will be used herein to designate any composition with which stable emulsions can be obtained very easily, for example, simply by hot dispersion under mechanical stirring.

Examples of such self-emulsifiable compositions are the CETOMAGROCOL EMULSIFYING WAX described in the British Pharmacopea or else the products sold under the denominations CIRE DE LANOL CTO (Company SEPPIC), SINNOWAX AO (Company HENKEL) or else PROMULGEN G (Company AMERCHOL).

These compositions are generally constituted by:

60 to 90% by weight of higher fatty alcohols ($C_{16}$–$C_{18}$);

10 to 40% by weight of cetylstearylic alcohol condensed with 20 to 35 molecules of ethylene oxide.

Fatty ester based waxes are also known, which waxes are made self-emulsifiable by the addition of polyoxylethylated fatty acid. One example of this type of product is the ARLACEL 165 (Company ICI) constituted by about 50% by weight of glycerol stearate and 50% by weight of stearic acid condensed with 100 molecules of ethylene oxide.

Said known self-emulsifiable compositions make it possible to obtain very easily emulsions which are very stable and can contain active, dispersed or dissolved molecules (analgesic, antibiotic, antiseptic, hydrating, antiultraviolet, hair conditioning, etc. . . . ) for example by hot dispersion (50 to 80° C.) in water or in suitable polar mediums, simply by slow mechanical stirring.

However, all said self-emulsifiable compositions are obtained by a method which includes an ethylene oxide condensation step, and therefore they are liable to contain impurities which are linked to that method, such as for example the 1,4-dioxane or the ethylene oxide which are generally considered as toxic products detrimental to health.

In these conditions, it is essentially the object of the present invention to solve the technical problem consisting in providing new fatty alcohol based self-emulsifiable compositions showing none of the aforesaid disadvantages.

It has been found, and this is the basis of the present invention, that fatty alcohol based compositions, comprising:

60 to 90% by weight of a fatty alcohol, having 12 to 22 carbon atoms;

10 to 40% by weight of an alkylpolyoside, the alkyl part of which is preferably identical to that of the fatty alcohol;

and, if appropriate, 0.5 to 5% by weight of polyosides, have the unexpected property of being self-emulsifiable and that such compositions can be advantageously used for preparing emulsions.

Thus, simply by hot dispersion in water or in a hydrophilic polyol, said compositions lead to stable emulsions, without having to resort to the conventional technology of emulsions in which a couple of emulsifiers are used (one being hydrophilic and the other lipophilic).

Such self-emulsifiable compositions can be obtained by methods which, contrary to those used heretofore, generate no toxic impurity.

It should be noted that the alkylpolyosides are non-ionic surface-active agents already used in a large range of industrial applications.

These compounds, however, have never been used as emulsifiers for preparing self-emulsifiable compositions.

Thus, in a first aspect, the object of the invention is to cover the use of fatty alcohol based compositions comprising:

60 to 90% by weight of at least one fatty alcohol having from 12 to 22 carbon atoms, preferably from 16 to 18 carbon atoms, 10 to 40% by weight of an alkylpolyoside, preferably an alkylpolyoside of which the alkyl part is identical to that of the fatty alcohol, and, if appropriate, 0.5 to 5% of polyoside for the preparation of emulsions.

In a second aspect, the object of the invention is to cover a method of preparing emulsions, characterized in that it comprises the steps of:

a) preparing a self-emulsifiable composition comprising:

60 to 90% by weight of at least one fatty alcohol having from 12 to 22 carbon atoms, preferably from 16 to 18 carbon atoms, 10 to 40% by weight of an alkylpolyoside, preferably an alkylpolyoside of which the alkyl part is identical to that of the fatty alcohol, and, if appropriate, 0.5 to 5% of polyoside; and b) hot-dispersing said composition, for example between about 50° C. and about 80° C., in water or in a suitable polar medium, by simple, slow, notably mechanical, stirring.

It should be noted that, at the industrial level, there are two principal synthesis methods for the alkylpolyosides.

The first method comprises reacting, in an acid medium, an alcohol and an ose having an anomeric OH, such as for example glucose or dextrose.

The second method consists:

in a first step, in preparing an alkylpolyoside with a lower alcohol such as for example glucose, in order to obtain known products such as methylglucoside or butylglucoside with a high yield; then in a second step, carrying out a transetherification with a higher fatty alcohol, having for example from 8 to 22 carbon atoms, with distillation of the lower alcohol (methanol or butanol).

It has been found, quite unexpectedly, that the mixtures of alkylpolyoside with higher fatty alcohol in excess, obtained by said first conventional synthesis method (without distillation), exhibited particularly advantageous self-emulsifiable properties.

This explains why, according to another particular characteristic of the invention, the self-emulsifiable compositions are obtained directly by reaction, in acid medium, of a fatty alcohol having from 12 to 22 carbon atoms with an ose, followed, if appropriate, by neutralization and filtration.

Understandably, the fatty alcohol is used in excess, so that the reaction product contains the above specified quantities of non-etherified fatty alcohols and of alkylpolyoside. It has also been found that it is also possible to obtain self-emulsifiable compositions just by mixing, in the hereinbefore indicated proportions, at least one fatty alcohol having from 12 to 22 carbon atoms, preferably from 16 to 18 carbon atoms, with an alkylpolyoside, of which the alkyl part is preferably identical to that of the fatty alcohol; which alkylpolyoside can be obtained by any known method and notably by the two main synthesis methods mentioned hereinabove.

Advantageously, said alkylpolyoside comprises at least one ose selected from the group constituted of glucose or dextrose, saccharose, fructose, galactose, maltose, maltotriose, lactose, cellobiose, mannose, ribose, dextrane, talose, allose, xylose, levoglucosane, cellulose and starch; preferably glucose, dextrose, fructose and maltose.

Generally, the polyoside chain comprises up to 30 units.

It should also be noted that each unit of the polyoside part can be in α or β isomeric form, in L or D form, and the conformation of the "ose" unit in furanoside or pyranoside form with an anomeric oxygen.

The alkylpolyosides used in the present invention are generally the ether-alkyls of polysaccharide (or oligosaccharide).

Moreover, the fatty alcohols which can be used for preparing the self-emulsifiable compositions according to the invention are generally linear or branched alcohols, of natural origin, such as for example alcohols from vegetable materials (copra, cabbage, palm) or animal materials (tallow); or else synthetic materials, the chain length of which is comprised between 12 and 22 carbon atoms, preferably between 14 and 22 carbon atoms.

It is understood that other long chain alcohols can also be used such as for example etheralcohols or the alcohols known as Guerbet's alcohols.

Finally, it is also possible to use certain more or less long cuts of alcohol of natural origin, such as for example, coco ($C_{12}$ to $C_{16}$) or tallow ($C_{16}$ to $C_{18}$) or diols or cholesterol type compounds.

According to a particularly preferred characteristic of the invention, said fatty alcohol contains from 14 to 22 carbon atoms and preferably consists in a mixture of alcohols having from 16 to 18 carbon atoms originating from tallow or copra.

It should also be noted that the self-emulsifiable compositions used or produced according to the invention generally are, after filtration of the products from the possible polycondensation of the oses, in the form of a solid, pasty or liquid wax, depending on the nature of the fatty alcohol used.

Examples of acid catalyst usable for preparing said self-emulsifiable compositions are the sulphuric, phosphoric, hydrochloric, hypophosphoric acids and mixtures thereof.

The quantity of acid catalyst used will be between about 0.001 and 0.05 mole per mole of ose monomer.

The quantity of catalyst can be used for controlling the reaction speed.

Moreover, the reaction temperature will be generally comprised between about 90 and about 120° C., and the reaction time will be between about 3 and about 6 hours, preferably between 4 and 5 hours.

In general, these reaction conditions, as well as the excess of fatty alcohol, can be easily determined by the man skilled in the art who knows the molecular weight of the fatty alcohol and of the ose used, as well as the quantity of non-etherified fatty alcohol to be obtained at the end of the reaction.

The nature of the fatty alcohol and of the ose will be as defined hereinabove.

In a third aspect, the object of the present invention is to cover emulsions characterized in that they are obtained with the aforesaid method.

Advantageously, said emulsions are obtained by hot dispersion of said compositions, for example between 50 and 80° C., in water or in a suitable polar medium such as for example a polyol, simply by slow stirring, notably mechanical stirring.

The emulsions that can be produced within the present invention are, for example, milks or creams, notably based on vegetable oil or waxes, polar oil, mineral oil and silicon oil.

In this respect, it has been, quite unexpectedly, found that the self-emulsifiable oils used according to the invention are better, as regards their emulsifying power, than the conventional emulsifying products, particularly towards the vegetable oils or the silicon oils which are very difficult to emulsify.

The invention will be illustrated in more details by the following examples, given solely by way of illustration and non-restrictively, and which, therefore, cannot in any way limit the scope of the invention.

In these examples, the percentages are expressed by weight, unless otherwise stated.

EXAMPLE 1

Preparation of a Self-Emulsifiable Composition 3 moles of tallow alcohol ($C_{16}$–$C_{18}$) and 1 mole of anhydrous glucose are reacted in the presence of a catalytic system constituted by sulfuric acid (1.5 g/kg) and hypophosphorous acid at 50% (2 g/kg). The reaction is conducted in vacuo, at a temperature of about 105° C., for 4 to 5 hours.

After neutralizing with soda, the reaction product is filtered and drained in order to remove the glucose polycondensates.

When the reaction is completed (sufficient time), there is virtually no glucose polycondensate left so that said neutralization is not necessary.

The product obtained with this method has a melting point of about 45° C. and its acid index is less than 1.

Said product has the following composition:

| | |
|---|---|
| Cetystearylic alcohol ($C_{16}$–$C_{18}$) | 87.2% |
| Cetearylglucosides | 12.2% |
| Glucose | 0.6% |

This product is found to be readily emulsifiable under heat (60–70° C.) in water, to give either a cream or a milk, depending on the quantities used.

By way of illustration, a cream and a milk were produced by mixing the quantities indicated hereunder.

| Cream: | |
|---|---|
| Self-emulsifiable composition of example 1: | 25% |
| water: | 75% |

This cream has a viscosity of about 25,000 cPs at 20° C.

Milk:

| | |
|---|---|
| Self-emulsifiable composition of example 1: | 5% |
| water | 95% |

This milk has a viscosity of about 3,200 cPs at 20° C.

It should be noted that the self-emulsifiable composition of example 1 is in the form of a wax and that the ocular and skin tolerance of this wax is perfect (the primary indications of eye and skin irritation being nil).

This self-emulsifiable composition is also free of toxic impurities such as 1,4-dioxane, free ethylene oxide or amines which can form nitrosamines.

EXAMPLE 2
Preparation of a Self-Emulsifiable Composition According to the Invention A self-emulsifiable wax having properties similar to those of Example 1 is obtained by replacing the tallow alcohol with oleic alcohol (bidistilled olein).

The product obtained has the following composition:

| | |
|---|---|
| Oleic alcohol | 81.3% |
| Oleylglucosides | 18% |
| Polydextrose | 0.7% |

EXAMPLE 3
Examples of Emulsions Obtainable from the Self-Emulsifiable Compositions According to Examples 1 and 2

1) Moisturizing cream for oily skins:

| | |
|---|---|
| Self-emulsifiable composition of example 1 (Wax I) | 5% (p/p) |
| Cetylstearyloctanoate | 8% |
| Octylpalmitate | 2% |
| Polyacrylamide (SEPIGEL 305) | 0.6% |
| Mucopolysaccharides (SOLABIA) | 5.0% |
| MICROPEARL M 100 | 3.0% |
| Preserving agent (SEPICIDE HB) | 0.8% |
| Perfume (Boretta PN 2305 Quest) | 0.2% |
| Distilled water | s.q.f. 100% |

Viscosity obtained: about 22,000 mPa at 25° C.

The emulsification is obtained just by melting of the Wax I and the fatty phase, which is mixed under slow mechanical stirring with the aqueous phase preheated to 60° C.

Said cream is stable at 25° C. and 40° C. for several months.

2) Untangling hair cream:

| | |
|---|---|
| Wax I | 2.8% |
| Cetyltrimethylammonium chloride (CTAC) | 3.0% |
| Kathon CG (preserving agent) | 0.1% |
| Perfume | 0.2% |
| Demineralized water | s.q.f. 100% |

A stable cream is obtained by simple emulsifying of the cationic untangling agent (CTAC) with the Wax I molten at 60° C. and mixed with water at that same temperature.

3) Make-up Removing Emulsion with Sweet Almond Oil

Vegetable oils are known to be difficult to emulsify.

The Wax I allow easy emulsifying of the sweet almond oil with excellent stability.

| | |
|---|---|
| Wax I | 5% |
| Sweet almond oil | 5% |
| Polyacrylamide (SEPIGEL 305) | 0.3% |
| Glycerin | 5% |
| Preserving agent | 0.2% |
| Perfume | 0.3% |
| Distilled water | s.q.f. 100% |

Aspect: shiny white cream.

| 4) Night cream: | |
|---|---|
| Wax I | 5% |
| Cetylstearyloctanoate | 10% |
| Octylpalmitate | 5% |
| Silicon oil (DC 200/350) | 2% |
| Palmitate glycol | 1% |
| Mucopolysaccharides | 5% |
| Micropearl M100 | 5% |
| Water | s.q.f. 100% |
| 5) Fluid emulsion (pomade base): | |
| Self-emulsifiable composition of example 2 (oleic) | 10% |
| Cetylstearyloctanoate | 5% |
| Preserving agent | 0.2% |
| Distilled water | s.q.f. 100% |

EXAMPLE 4
A) Preparation of a Self-Emulsifiable Composition 80 g of a mixture of fatty alcohols (C12: 25%; C14: 25%; C16: 25%; C18: 25%) are reacted with 20 g of butylglucoside (sold under the trademark ORAMIX BG 14 by SEPPIC—FRANCE) at 80° C. in the presence of sulfuric acid at pH=1, for 3 hours, while distilling the butanol which forms. The transetherification leads to the following reaction composition:

Fatty alcohol ($C_{12}$ to $C_{18}$): 64.3%

Alkyl ($C_{12}$ to $C_{18}$) glucosides: 33.8%

Butylglucoside: 1.9%

The product obtained is readily emulsifiable in water to give, under mechanical stirring, an emulsion of varying consistency.

B) Examples of Use of the Self-Emulsifiable Composition thus Prepared a—Fluid and unctuous milk of viscosity 2800 cPs, obtained by mixing:

7% product according to A

93% demineralized water b—Thick and stable cream of viscosity 75,000 cPs, obtained by mixing:

21% product according to A

79% demineralized water.

We claim:

1. A method for preparing an emulsion comprising:

a) a first step of separately forming a self-emulsifiable composition as a reaction product by reacting, in acid medium, at least one fatty alcohol having from 12 to 22 carbon atoms with at least one ose selected from the group consisting of glucose, dextrose, saccharose, fructose, galactose, maltose, maltotriose, lactose, cellobiose, mannose, ribose, dextrane, talose, allose, xylose, levoglucosane, cellulose and starch in reaction conditions such that the reaction product consists essentially of 60 to 90% by weight of at least one fatty alcohol having from 12 to 22 carbon atoms, 10 to 40% by weight of an alkylpolyoside of which the alkyl part is identical to that of the fatty alcohol, and from 0 to 5% by weight of polyoside and such that the composition can form a stable emulsion merely by dispersion of a sufficient quantity of the composition at a temperature between about 50 and 80 degrees C. in an aqueous phase; and b) a subsequent step of dispersing the composition obtained in step a at said temperature in the aqueous phase in a sufficient quantity to form a stable emulsion.

2. A method according to claim 1, wherein said dispersing step (b) is carried out by mechanical stirring.

3. A method according to claim 1, wherein the fatty alcohol used in step a) for preparing said composition has from 14 to 22 carbon atoms and consists of a mixture of alcohols naturally occurring in tallow.

4. A method for preparing emulsions as claimed in claim 1 wherein the method consists essentially of said steps a and b.

5. A method for preparing emulsions as claimed in claim 1 wherein the fatty alcohol has from 16 to 18 carbon atoms.

6. A method as claimed in claim 1 wherein the reaction product in step a is a solid, pasty or liquid wax.

7. A method as claimed in claim 6 comprising including in said emulsion an oil selected from the group consisting of vegetable oil, polar oil, mineral oil and silicon oil.

8. A method as claimed in claim 7 wherein the oil is a vegetable oil.

9. A method as claimed in claim 7 wherein the oil is a silicon oil.

10. A method as claimed in claim 1 wherein the at least one fatty alcohol is present in said acid medium in a mixture of alcohols, said mixture of alcohols consisting of at least 50% by weight of alcohols having from 16 to 18 carbon atoms.

11. A method for preparing an emulsion comprising:
a) a first step of separately forming a self-emulsifiable composition as a reaction product by reacting, in acid medium, at least one fatty alcohol having from 12 to 22 carbon atoms with at least one ose selected from the group consisting of glucose, dextrose, saccharose, fructose, galactose, maltose, maltotriose, lactose, cellobiose, mannose, ribose, dextrane, talose, allose, xylose, levoglucosane, cellulose and starch in reaction conditions such that the reaction product consists essentially of 60 to 90% by weight of at least one fatty alcohol having from 12 to 22 carbon atoms, 10 to 40% by weight of an alkylpolyoside, of which the alkyl part is identical to that of the fatty alcohol, and from 0 to 5% by weight of polyoside and such that the composition can form a stable emulsion merely by dispersion of a sufficient quantity of the composition at a temperature between about 50 and 80 degrees C. in an aqueous phase;

a1) neutralizing and filtering the composition thus obtained, and b) a subsequent step of dispersing the neutralized and filtered composition at said temperature in the aqueous phase in a sufficient quantity to form a stable emulsion.

12. A method according to claim 11, wherein said dispersing step (b) is carried out by mechanical stirring.

13. A method according to claim 11, wherein the fatty alcohol used in step (a) for preparing said composition has from 14 to 22 carbon atoms and consists of a mixture of alcohols naturally occurring in tallow.

14. A method as claimed in claim 11 wherein the reaction product in step a is a solid, pasty or liquid wax.

15. A method as claimed in claim 14 comprising including in said emulsion an oil selected from the group consisting of vegetable oil, polar oil, mineral oil and silicon oil.

16. A method as claimed in claim 15 wherein the oil is a vegetable oil.

17. A method as claimed in claim 15 wherein the oil is a silicon oil.

18. A method as claimed in claim 11 wherein the at least one fatty alcohol is present in said acid medium in a mixture of alcohols, said mixture of alcohols consisting of at least 50% by weight of alcohols having from 16 to 18 carbon atoms.

19. A method according to claim 1, wherein the fatty alcohol used in step a) for preparing said composition has from 14 to 22 carbon atoms and consists of a mixture of alcohols naturally occurring in copra.

20. A method according to claim 11, wherein the fatty alcohol used in step a) for preparing said composition has from 14 to 22 carbon atoms and consists of a mixture of alcohols naturally occurring in copra.

21. A method for preparing an emulsion comprising:
a) a first step of separately forming a self-emulsifiable composition as a reaction product by reacting, in acid medium, a mixture of fatty alcohols consisting of at least 50% by weight of fatty alcohols having from 16 to 18 carbon atoms with at least one ose selected from the group consisting of glucose, dextrose, saccharose, fructose, galactose, maltose, maltotriose, lactose, cellobiose, mannose, ribose, dextrane, talose, allose, xylose, levoglucosane, cellulose and starch in reaction conditions such that the reaction product consists essentially of 60 to 90% by weight of fatty alcohols from said mixture including at least one fatty alcohol having from 16 to 18 carbon atoms, 10 to 40% by weight of alkylpolyosides with at least one alkylpolyoside having an alkyl part identical to that of the at least one fatty alcohol, and from 0 to 5% by weight of polyoside and such that the composition can form a stable emulsion merely by dispersion of a sufficient quantity of the composition at a temperature between about 50 and 80 degrees C. in an aqueous phase; and b) a subsequent step of dispersing the composition obtained in step a at said temperature in the aqueous phase in a sufficient quantity to form a stable emulsion.

22. A method for preparing an emulsion comprising:
a) a first step of separately forming a self-emulsifiable composition as a reaction product by reacting, in acid medium, a mixture of fatty alcohols consisting of at least 50% by weight of fatty alcohols having from 16 to 18 carbon atoms with at least one ose selected from the group consisting of glucose, dextrose, saccharose, fructose, galactose, maltose, maltotriose, lactose, cellobiose, mannose, ribose, dextrane, talose, allose, xylose, levoglucosane, cellulose and starch in reaction conditions such that the reaction product consists essentially of 60 to 90% by weight of fatty alcohols from said mixture including at least one fatty alcohol having from 16 to 18 carbon atoms, 10 to 40% by weight of alkylpolyosides with at least one alkylpolyoside having an alkyl part identical to that of the fatty at least one fatty alcohol, and from 0 to 5% by weight of polyoside and such that the composition can form a stable emulsion merely by dispersion of a sufficient quantity of the composition at a temperature between about 50 and 80 degrees C. in an aqueous phase;

a1) neutralizing and filtering the composition thus obtained, and b) a subsequent step of dispersing the composition obtained in step a at said temperature in the aqueous phase in a sufficient quantity to form a stable emulsion.

23. A method as claimed in claim 1, wherein the composition in step a is present in the stable emulsion in an amount of at least about 2.8% by weight.

24. A method as claimed in claim 11, wherein the composition obtained in step a is present in the stable emulsion in an amount of between about 5–25% by weight.

25. A method as claimed in claim 1, wherein the composition obtained in step a is present in the stable emulsion in an amount sufficient to form a milk or cream when dispersed in the water or polyol.

26. A method as claimed in claim 1, wherein in step b, the composition obtained in step a is dispersed in a liquid consisting essentially of the water or polyol.

27. A method for preparing an emulsion consisting essentially of
a) separately forming a self-emulsifiable composition as a reaction product by reacting, in acid medium, at least one fatty alcohol having from 12 to 22 carbon atoms with at least one ose selected from the group consisting of glucose, dextrose, saccharose, fructose, galactose, maltose, maltotriose, lactose, cellobiose, mannose, ribose, dextrane, talose, allose, xylose, levoglucosane, cellulose and starch in reaction conditions such that the reaction product consists essentially of 60 to 90% by weight of at least one fatty alcohol having from 12 to 22 carbon atoms, 10 to 40% by weight of an alkylpolyoside of which the alkyl part is identical to that of the fatty alcohol, and from 0 to 5% by weight of polyoside and such that the composition can form a stable emulsion merely by dispersion of a sufficient quantity of the composition at a temperature between about 50 and 80 degrees C. in an aqueous phase; and
b) dispersing the composition obtained in step a, and optionally also dispersing an oil, at said temperature in the aqueous phase, said composition obtained in step a being dispersed in the aqueous phase in a sufficient quantity to form a stable emulsion.

28. A method as claimed in claim 27, wherein the reaction product in step a) is a wax.

29. A method as claimed in claim 28, wherein the composition and the oil are dispersed in the aqueous phase in step (b), said oil being selected from the group consisting of vegetable oil, polar oil, mineral oil and silicon oil.

30. A method as claimed in claim 29, wherein the oil is a vegetable oil.

31. A method as claimed in claim 29, wherein the oil is a silicon oil.

32. A method as claimed in claim 27, wherein the at least one fatty alcohol is present in said acid medium in a mixture of alcohols, said mixture of alcohols consisting of at least 50% by weight of alcohols having from 16 to 18 carbon atoms.

33. A method according to claim 27, wherein the fatty alcohol used in step a) for preparing said composition has from 14 to 22 carbon atoms and consists of a mixture of alcohols naturally occurring in copra.

34. A method for preparing an emulsion consisting essentially of
a) separately forming a self-emulsifiable composition consisting essentially of 60 to 90% by weight of at least one fatty alcohol having from 12 to 22 carbon atoms, 10 to 40% by weight of an alkylpolysoide of which the alkyl part is identical to that of the fatty alcohol, and from 0 to 5% by weight of polyoside; and
b) dispersing the composition obtained in step a), and optionally also dispersing an oil, at a temperature between about 50 and 80 degrees C. in an aqueous phase, said composition obtained in step a being dispersed in the aqueous phase in a sufficient quantity to form a stable emulsion.

35. A method as claimed in claim 34, wherein the self-emulsifiable composition in step a) is formed as a reaction product by transetherifying a lower alkylpolyoside with at least one fatty alcohol in reaction conditions such that the reaction product consists essentially of 60 to 90% by weight of at least one fatty alcohol having from 12 to 22 carbon atoms, 10 to 40% by weight of an alkylpolyoside of which the alkyl part is identical to that of the fatty alcohol, and from 0 to 5% by weight of the polyoside.

36. A method as claimed in claim 35, wherein the reaction product instep a) is a wax.

37. A method as claimed in claim 36, wherein the composition and the oil are dispersed in the aqueous phase in step b), said oil being selected from the group consisting of vegetable oil, polar oil, mineral oil and silicon oil.

38. A method as claimed in claim 37, wherein the oil is a vegetable oil.

39. A method as claimed in claim 37, wherein the oil is a silicon oil.

40. A method as claimed in claim 35, wherein the at least one fatty alcohol is present in said acid medium in a mixture of alcohols, said mixture of alcohols consisting of at least 50% by weight of alcohols having from 16 to 18 carbon atoms.

41. A method according to claim 35, wherein the fatty alcohol used in step a) for preparing said composition has from 14 to 22 carbon atoms and consists of a mixture of alcohols naturally occurring in copra.

42. A method for preparing an emulsion consisting essentially of
a) separately forming a self-emulsifiable composition as a reaction product by reacting, in acid medium, at least one fatty alcohol having from 12 to 22 carbon atoms with at least one ose selected from the group consisting of glucose, dextrose, saccharose, fructose, galactose, maltose, maltotriose, lactose, cellobiose, mannose, ribose, dextrane, talose, allose, xylose, levoglucosane, cellulose and starch in reaction conditions such that the reaction product consists essentially of 60 to 90% by weight of at least one fatty alcohol having from 12 to 22 carbon atoms, 10 to 40% by weight of an alkylpolyoside of which the alkyl part is identical to that of the fatty alcohol, and from 0 to 5% by weight of polyoside and such that the composition can form a stable emulsion merely by dispersion of a sufficient quantity of the composition at a temperature between about 50 and 80 degrees C. in an aqueous phase,
a1) neutralizing and filtering the composition thus formed; and
b) dispersing the neutralized and filtered composition, and optionally also dispersing an oil, at said temperature in the aqueous phase, said neutralized and filtered composition being dispersed in the aqueous phase in a sufficient quantity to form a stable emulsion.

43. A method as claimed in claim 42, wherein the reaction product in step a) is a wax.

44. A method as claimed in claim 43, wherein the composition and the oil are dispersed in the aqueous phase in step (b), said oil being selected from the group consisting of vegetable oil, polar oil, mineral oil and silicon oil.

45. A method as claimed in claim 44, wherein the oil is a vegetable oil.

46. A method as claimed in claim 44, wherein the oil is a silicon oil.

47. A method as claimed in claim 42, wherein the at least one fatty alcohol is present in said acid medium in a mixture of alcohols, said mixture of alcohols consisting of at least 50% by weight of alcohols having from 16 to 18 carbon atoms.

48. A method as claimed in claim 42, wherein the fatty alcohol used in step a) for preparing said composition has from 14 to 22 carbon atoms and consists of a mixture of alcohols naturally occurring in copra.

49. A method for preparing an emulsion consisting essentially of
- a) separately forming a self-emulsifiable composition consisting essentially of 60 to 90% by weight of at least one fatty alcohol having from 12 to 22 carbon atoms, 10 to 40% by weight of an alkylpolysoide of which the alkyl part is identical to that of the fatty alcohol, and from 0 to 5% by weight of polyoside; and
- a1) neutralizing and filtering the composition thus formed; and
- b) dispersing the neutralized and filtered composition, and optionally also dispersing an oil, at a temperature between about 50 and 80 degrees C. in an aqueous phase, said neutralized and filtered composition being dispersed in the aqueous phase in a sufficient quantity to form a stable emulsion.

50. A method as claimed in claim 49, wherein the self-emulsifiable composition in step a) is formed as a reaction product by transetherifying a lower alkylpolyoside with at least one fatty alcohol in reaction conditions such that the reaction product consists essentially of 60 to 90% by weight of at least one fatty alcohol having from 12 to 22 carbon atoms, 10 to 40% by weight of an alkylpolyoside of which the alkyl part is identical to that of the fatty alcohol, and from 0 to 5% by weight of the polyoside.

51. A method as claimed in claim 50, wherein the reaction product in step a) is a wax.

52. A method as claimed in claim 51, wherein the composition and the oil are dispersed in the aqueous phase in step b), said oil being selected from the group consisting of vegetable oil polar oil, and silicon oil.

53. A method as claimed in claim 52, wherein the oil is a vegetable oil.

54. A method as claimed in claim 52, wherein the oil is a silicon oil.

55. A method as claimed in claim 50, wherein the at least one fatty alcohol is present in said acid medium in a mixture of alcohols, said mixture of alcohols consisting of at least 50% by weight of alcohols having from 16 to 18 carbon atoms.

56. A method as claimed in claim 50, wherein the fatty alcohol used in step a) for preparing said composition has from 14 to 22 carbon atoms and consists of a mixture of alcohols naturally occurring in copra.

* * * * *